United States Patent
Renirie et al.

[11] Patent Number: 6,141,590
[45] Date of Patent: Oct. 31, 2000

[54] SYSTEM AND METHOD FOR RESPIRATION-MODULATED PACING

[75] Inventors: Alexis C. M. Renirie, AC Berg en Dal; Vincent J. A. Schouten, ET Cadier en Keer, both of Netherlands

[73] Assignee: Medtronic, Inc., Minneapolis, Minn.

[21] Appl. No.: 08/937,443

[22] Filed: Sep. 25, 1997

[51] Int. Cl.$^7$ .................................................. A61N 1/365
[52] U.S. Cl. ............................................. 607/20; 607/18
[58] Field of Search .................................. 607/9, 17, 20, 607/23, 24, 18, 19

[56] References Cited

U.S. PATENT DOCUMENTS

| | | |
|---|---|---|
| 4,510,944 | 4/1985 | Porges . |
| 4,721,110 | 1/1988 | Lampadius ................................. 607/20 |
| 4,896,675 | 1/1990 | Ohsuga et al. . |
| 4,960,129 | 10/1990 | dePaola et al. . |
| 4,972,842 | 11/1990 | Korten et al. . |
| 5,266,070 | 11/1993 | Hagiwara et al. . |
| 5,466,245 | 11/1995 | Spinelli et al. . |
| 5,964,788 | 11/1999 | Greenhut ................................. 607/20 |

FOREIGN PATENT DOCUMENTS 0 753 324 A1  1/1997  Sweden .

OTHER PUBLICATIONS

Paul Grossman et al. "Respiratory Sinus Arrhythmia as an Index of Parasympathetic Cardiac Control During Active Coping", Psychophysiology, vol. 24, No. 2, Mar. 1987, pp. 228–235.

*Primary Examiner*—George R. Evanisko
*Attorney, Agent, or Firm*—Thomas F. Woods; Harold Patton; Michael J. Jaro

[57] ABSTRACT

A system and method of providing for cardiac pacing which incorporates modulation of the pacing rate in order to minimize variations in ventricular power output, e.g., variation related to patient respiratory phases. In a preferred embodiment, pacing rate is increased during inspiration relative to expiration, to restore a measure of the normal rate modulation which occurs in a normal person. Patient respiration is monitored and a respiration signal is processed to determine the timing of rate modulation. Parameters representative of respiratory changes, such as right ventricular volume and right ventricular blood pressure are also monitored and, together with respiration amplitudes changes, are used to determine an incremental rate signal for controlling the extent of rate variation. Heart rate and patient activity are also sensed, to provide further control of rate modulation, with maximum modulation being provided when the patient is sleeping, and minimal or no modulation being provided when the patient is active. The system of this invention is applicable in combination with conventional pacing systems, or can be adapted to special clinical applications.

28 Claims, 6 Drawing Sheets

SYSTEM AND METHOD FOR RESPIRATION-MODULATED PACING

FIELD OF THE INVENTION

This invention relates to cardiac pacing systems and, in particular, to pacing systems which provide rate modulation of pacing pulses based upon monitored patient respiratory phases.

BACKGROUND OF THE INVENTION

It is known that in a normal human patient, there are respiration-induced variations in heart rate. These variations are known as respiratory sinus arrhythmia (RSA). However, in certain patients, the normal respiratory phasic modulation of heart rate may be lacking. For example, in a patient with a conventional pacemaker, e.g., atrial pacing for bradycardia, the respiratory control is missing. There are also cases where improved hemodynamics by respiration-modulated pacing can be beneficial to patients with heart failure. For example, sleep-disordered breathing (periodic or Cheyne-Stokes respiration) is common in patients with advanced stages of heart failure. There are suggestions in the literature that the impaired circulation and heart function may be a causal factor in the development of this breathing disorder, and that improved hemodynamics leads to improved breathing. Accordingly, the advantage of restoring respiration-modulated rate variations may be beneficial to such patients.

Respiratory sinus arrhythmia is also suppressed in patients with severe hypertension due to a low parasympathetic activity. Regardless of the initiating cause of hypertension, the poor RSA and the ensuing variability in ventricular power output may well contribute to the perpetuation of hypertension. Thus, the restoration of RSA may be beneficial to many hypertensive patients. After thoracic surgery, patients are often artificially ventilated and under the influence of sedatives for several days, which condition frequently leads to complications such as atelectasis (fluid accumulation in the lower lung lobes). The complications are due to the positive pressure ventilation which tends to squeeze blood from the lungs and impairs the pulmonary circulation. For such patients, improved respiration-coupled heart rate modulation may aid in normalizing circulation.

It is important to understand the mechanism by which the normal body modulates cardiac rate in accordance with the inspiration/expiration cycle, and the benefit of such modulation. During expiration the relatively high thoracic pressure causes compression of the Vena Cava and a reduction of blood flow toward the right atrium. During inspiration and relative negative pressure the Vena Cava expands and the flow of venous blood to the right atrium increases. This cyclic variation in venous return results in a marked beat-to-beat variation in the stroke volume and power output of the right ventricle. The cyclic variation in heart rate is an adaptation which tends to make the stroke volume and power output per beat more constant. In the elderly and in patients with chronic diseases such as diabetes, heart failure or hypertension, the control of circulation is impaired due to reduced function of the autonomic nervous system. Consequently, the respiration-induced variations in heart rate are much smaller for these patients than for healthy subjects, causing variations in power output and oxygen consumption of the heart. The variable power input into the large arteries may have long-term effects on the vascular walls. This in turn may contribute to the progression of chronic diseases, pulmonary or systemic hypertension and right ventricular failure in particular. Accordingly, the restoration of a respiratory-modulated cardiac rate, by means of an implanted device, would improve this condition for patients with conditions such as hypertension and heart failure, and would provide an additional benefit in conventional pacemaker applications. Further, the advantage may be utilized by an external system for post-surgery, artificially-ventilated patients.

The variation of return of venous blood to the ventricles during respective respiratory phases is an important factor underlying respiratory modulation of heart rate. Inspiration has opposite effects on the pump functions of the right and left ventricles. The decreased intrathoracic pressure during inspiration causes a marked increase in the return of venous blood from the body into the right atrium, and a large end-diastolic volume in the right ventricle. The inspiratory expansion of the lungs leads to an accumulation of blood in the expanding lung vessels and a reduced flow of blood into the left atrium and ventricle, i.e., decreased pre-load. Thus, there is a respiration-induced tidal-type shift of blood volume back and forth between the peripheral and the pulmonary circulation, which causes variations in the pre-load and output of both ventricles.

The enhanced return of blood into the right ventricle during inspiration, and the associated large end-diastolic volume of the RV, inhibits the filling of the left ventricle, because the ventricles share the septum and are mechanically coupled. However, an increased heart rate during inspiration, producing a shorter diastole, reduces somewhat the right ventricular end-diastolic volume, and the inhibition of left ventricle filling. As discussed in greater detail below, an increased heart rate during the inspiration phase makes the power output per beat from the right ventricle more constant. The increased venous return and the increased heart rate during inspiration lead to a rapid filling of the vessels in the expanded lungs. This amplifies the blood pumping action of the lungs. Thus, during inspiration a large amount of blood is pumped into the lung vessels at a low pressure, and a larger amount of blood is stored in the lung vessels. During expiration, the output from the right ventricle is relatively low, and the compression of the lung vessels pumps the stored blood into the left atrium and ventricle. The net effect is a more constant flow of blood into the left atrium during the entire respiratory cycle, part of the required energy being supplied by the mechanics of respiration. The more constant end-diastolic volume of the left ventricle implies a more constant power output per beat, and a more constant oxygen consumption. This is of particular importance to the left ventricle in which myocardial perfusion and oxygen supply is limited to the diastolic periods.

The right ventricle is suitably regarded as a volume pump, providing a volume of blood to the lungs. Its muscular wall is relatively thin and unable to produce high pressures. The power output (pressure×flow) is only about 15% of that of the left ventricle. The RV is well-adapted to pump blood through the pulmonary vessels which have a relatively low resistance. Inspiration, as opposed to expiration, is associated with a relatively low intra-thoracic pressure, increased venous return to the right atrium, large end-diastolic volume of the right ventricle, and a large stroke volume. Accordingly, the power output per beat is relatively high during inspiration. The higher heart rate during inspiration yields a shorter diastole, and thus reduces the end-diastolic volume and power output per beat, resulting in a more constant power output.

The situation with respect to the left ventricle is altered by its relative position with respect to the lungs. The expanding lung vessels retain blood during inspiration, and consequently the flow to the left atrium is relatively small. At the same time, the large volume of the right ventricle inhibits left ventricular filling. Both of these effects lead to a small end-diastolic volume of the left ventricle during inspiration. This is, however, counteracted by the increased heart rate which reduces the two above effects. Therefore, the result of a normal RSA is a more constant power output. This is beneficial, since variation of the amount of power stored per beat in the aorta and the pulmonary artery may influence the properties of the arterial walls and play a role in the development or maintenance of hypertension.

RSA is most prominent in supine resting subjects, in particular during deep, non-REM sleep, whereas it is absent during intensive exercise or in general when the heart rate is high. This is related to the balance between sympathetic and parasympathetic influences on the heart. In resting conditions, the parasympathetic influence (via the vagus nerve) dominates and the heart rate is relatively low. During exercise, the sympathetic influence causes a high heart rate and strong contractions.

In view of the above, it is seen that patients in whom the normal RSA is impaired may receive substantial benefit by the restoration of this function so as to provide a relative increase of heart rate during inspiration and relative decrease of heart rate during expiration. A solution to the problem for such patients has not been previously addressed. Reference is made to U.S. Pat. No. 4,791,931, which proposes an artificial baroreflex system comprising a pacemaker with an arterial blood pressure (ABP) sensor. The ABP sensor provides ABP signals which are used by the implantable device to adjust the pacing rate, whereby the pacing rate adjusts to the physiologic baroreflex mechanism. However, this system does not in any way take into account the respiratory phases, and does not provide for rate variations which alter the power output of the ventricles. Respiration signals have been used in rate-adaptive pacemakers, for the limited purpose of increasing heart rate during exercise. However, such applications respond only slowly to respiration frequency, and do not provide in any sense the type of respiration modulation required to restore the RSA function. Accordingly, for patients with impaired RSA function there remains a need for restoration of some measure of the RSA function.

SUMMARY OF THE INVENTION

It is an object of this invention to provide a system and method for stimulating a patient so as to provide cardiac rate modulation corresponding to a normal respiratory sinus arrhythmia, i.e., respiratory phasic rate variation. It is consequently an object to provide an implantable system for increasing the patient's heart rate during phases of inspiration relative to the patient's heart rate during phases of expiration.

In accordance with the above object, there is provided a system for respiration-modulated pacing, providing rate control for controlling the rate of generating and delivering stimulus pulses to correspond to the sensed inspiration and expiration phases of the patient's respiratory cycle. A respiration sensor obtains respiration signals representative of the amplitude and timing of patient respiration, which are used for developing rate modulation signals for controlling delivery of stimulus pulses. In addition, right ventricular blood pressure and right ventricular volume are monitored, for deriving further control signals used in determining the degree of phasic rate modulation. In one embodiment, the rate modulated stimulus signals are delivered to the patient's heart in the manner of conventional cardiac pacing, with an increased rate during inspiration. In a variation of the first embodiment, the pacing rate may be decreased during expiration as well. In yet another embodiment, the stimulus pulses may be delivered to the vagus nerve, or parasympathetic nervous system during expiratory phases, to produce a relative decrease of cardiac rate during expiration phases. In still another embodiment, stimulus pulses are delivered to the sympathetic nervous system during inspiratory phases.

DESCRIPTION OF THE PREFERRED EMBODIMENTS

Figure 1:
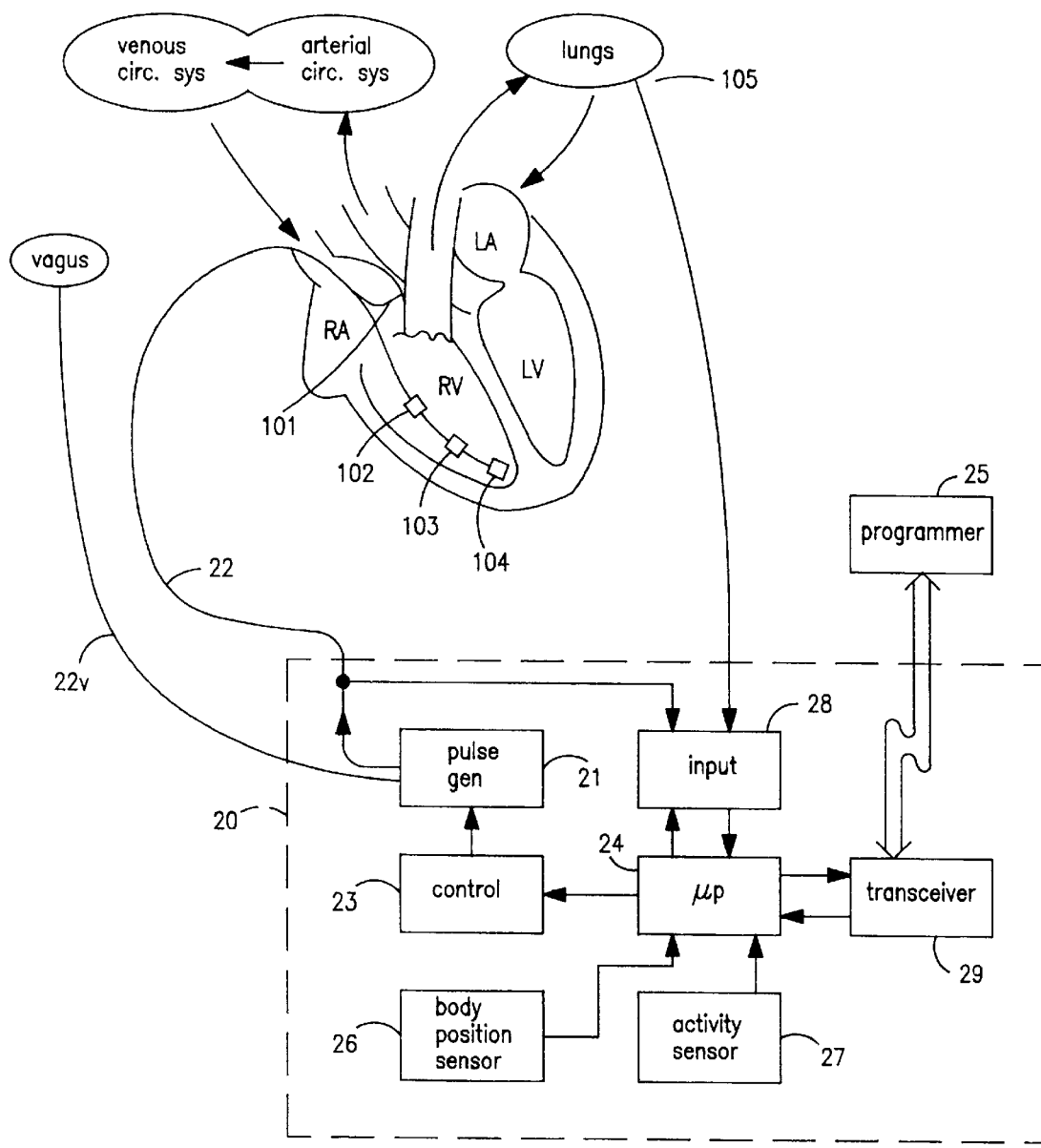
FIG. 1 is a schematic diagram illustrating the heart, the pulmonary and peripheral circulatory systems, as well as an implantable device for providing respiration-modulated pacing.

Referring to FIG. 1, there is illustrated an implantable pacemaker device 20, which provides conventional pacing functions and is also modified to provide phasic, respiration-modulated pacing in accordance with this invention. Pulse generator 21 generates pace stimulus pulses which are delivered across lead 22 in a conventional manner to the patient's heart. The pacing pulses may be delivered at atrial electrodes shown at 101, and/or at ventricular electrodes shown at 104. An alternate lead, shown schematically at 22V, can be employed to deliver stimulation to the vagal nerve. As used herein, the term pacing or cardiac pacing refers to delivering stimulus pulses to any heart chamber, or to a nerve by which heart rate can be controlled. Generation of pace pulses is controlled by control function block 23, which in a preferred embodiment receives timing and other logic signals from microprocessor block 24. As is well known in the pacemaker art, microprocessor 24 contains not only a hardware microprocessor, but also contains suitable memory, RAM and ROM, and can carry out its operations with any combination of hardware and software as desired. Block 24 is in communication with an external programmer 25, through transceiver 29, to receive programming instructions and to download diagnostic data. The device receives input data through input block 28, which provides suitable filtering and amplification, in a well-known manner. Input block 28 provides processed signal data to a microprocessor 24, and receives control instructions from it. As discussed in much greater detail in connection with FIG. 5 below, the input signals include signals representative of the patient EKG from which cardiac signal parameters are obtained; RV volume, suitably obtained from an impedance sensor 102 at or near the distal end of lead 22; and RV blood pressure, likewise suitably obtained from a sensor 103 carried by the lead. In addition, a respiration sensor 105, suitably an intrathoracic pressure sensor, is utilized to obtain signals representative of the respiratory cycle. Alternately, sensor 105 can measure lung volume, or a related variable. Additional input signals are obtained from a body position sensor 26, and an activity sensor 27, the outputs of which are coupled to microprocessor block 24.

Figure 2A:
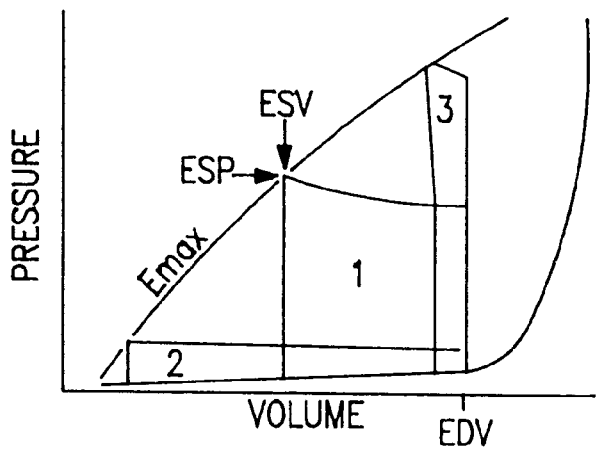
FIG. 2A is a schematic representation of pressure-volume loops in a ventricle.

Referring now to FIG. 2A, there is shown a schematic representation of pressure-volume loops in a ventricle. Starting from a given end-diastolic volume (EDV) point, at the time of systole the ventricle contracts and develops pressure. When this ventricular pressure exceeds arterial pressure, the valves open and blood is ejected, following which the ventricle returns to the EDV point. In a normal heart, the ventricle follows the loop shown diagrammatically at 1, where systole results in an initial upward jump of pressure, followed by decreasing volume and more gradual increase of pressure to the end-systolic points, ESP and ESV. When the blood has been ejected, pressure drops quickly and the volume then expands until the ventricle returns to the starting EDV point. For a patient with high arterial pressure, loop 3 would be a limiting condition where there is very little decrease in volume at systole, and the loop is almost a vertical jump up to the end-systolic point. At the other extreme, the limit is represented by very low arterial pressure, where stroke volume is maximum but pressure change is minimum. The $E_{max}$ curve represents a continuum of end-systolic points for variations of arterial pressure from minimum to maximum. The difference between ESV and EDV is referred to as the stroke volume, and for a normal ventricle is about 0.6×EDV.

Figure 2B:
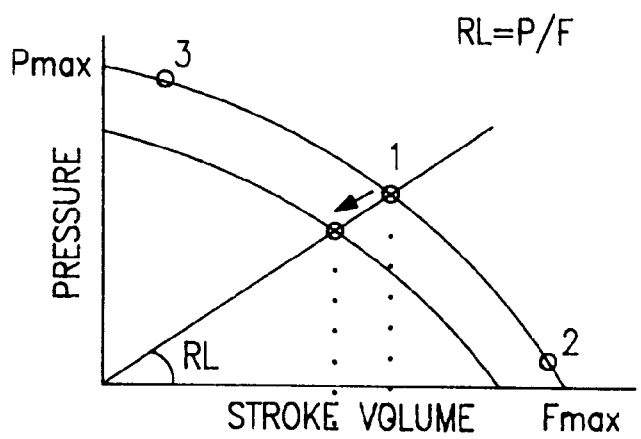
FIG. 2B is a draft of ventricular mean pressure vs. stroke volume per beat, showing the difference as a function of cardiac rate.

Referring to FIG. 2B, there is shown a graph of mean pressure vs. stroke volume per beat, adapted from the P-V loops of FIG. 2A. The numbered points on the solid curve correspond to the loops 1, 2, 3 of FIG. 2A. The dashed curve indicates the effect of increased heart rate. Note that an increased heart rate results in a shorter diastolic interval, which causes a smaller end-diastolic volume, and therefore a smaller stroke volume. Stated differently, when rate is increased, the ventricle cannot fill as far, so EDV and F (dV/dt) are less. The operation of the heart is presumed to vary along the straight dashed line designated RL, which is the peripheral resistance (pressure/stroke volume). As indicated, the operation point for the normal heart moves to a point of somewhat less stroke volume and mean pressure for a higher rate.

Figure 2C:
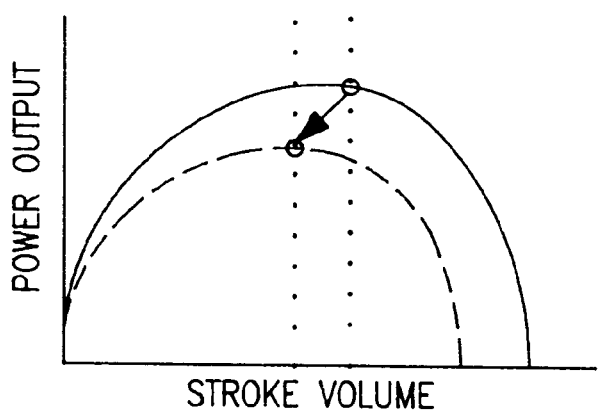
FIG. 2C shows a pair of graphs illustrating power output vs. stroke volume, again showing the difference in power output as a function of cardiac rate.

Referring to FIG. 2C, the solid line represents the product of pressure and stroke volume derived from FIG. 2B, which reflects the area of the respective P-V loops of FIG. 2A. It is seen that the work, at a given contractility and heart rate, is maximum at about 60% of the maximum stroke volume, which is where the ventricle is normally operating. The dashed line indicates the effect of increased heart rate, indicating a decrease of power output per beat resulting from an increase in heart rate.

Figure 3A:
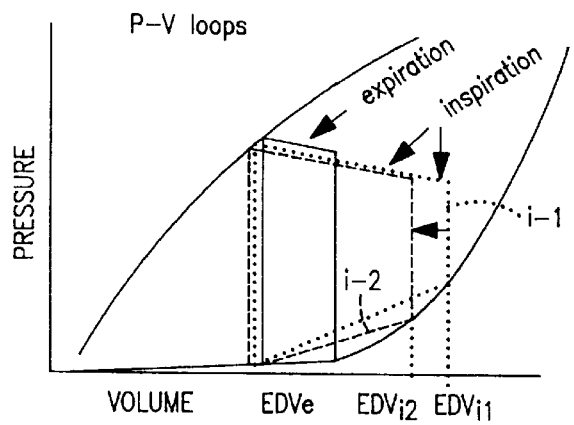
FIG. 3A shows pressure-volume loops for the right ventricle, illustrating the difference between inspiration and expiration.
Figure 3B:
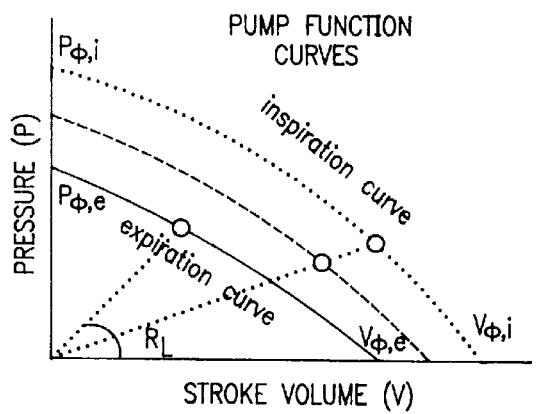
FIG. 3B shows pump function curves, for the right ventricle.
Figure 3C:
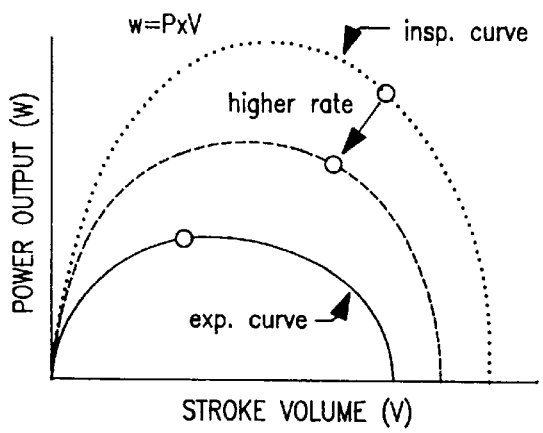
FIG. 3C shows power vs. stroke volume curves for the right ventricle.

With the principles of FIG. 2A–2C in mind, FIGS. 3A–C and 4A–C illustrate the different effects of rate on the right ventricle (RV) and left ventricle (LV), respectively. Referring to FIGS. 3A–3C, there are shown the same set of curves as FIGS. 2A–2C, but particularized for the right ventricle, and illustrating the effect of respiration and heart rate. It is to be remembered that for the right ventricle, the primary influence of inspiration is increased return of venous blood from the body and thus an increase of blood flow into, and blood storage in the lungs, which is characterized by a greater right ventricular stroke volume, and resultant greater power output. As seen in this series of curves, the consequence of an increased rate during inspiration is to reduce the power output to a level closer to that during expiration.

Referring to FIG. 3A, the expiration loop, indicated with solid lines, occurs when the venous return is low and the impedance of the lung vessels is relatively high, resulting in a relatively small end-diastolic volume, EDVe. The relatively small loop reflects relatively low overall work, or power output, as seen in FIG. 3C. The dotted loop identified as i-1 corresponds to a time of inspiration, and high venous return and low lung vessel impedance. Note that the end diastolic volume, $EDV_{i-1}$ is relatively large. The dashed loop, identified as i-2, reflects conditions with an increased heart rate, where the right ventricle does not have as much time to fill fully, resulting in a somewhat decreased $EDV_{i-2}$ smaller P-V loop. Referring to FIG. 3B, the pump function curves, it is seen that the inspiration curve is to the outside of the expiration curve, reflecting a wider range of stroke volumes. The ratio of pressure to stroke volume, RL, is lower during inspiration due to the expanded thoracic cage. As indicated, largely for this reason, during expiration stroke volume is much lower than during inspiration. When rate is increased, as seen in the dashed line, the inspiration curve moves toward the expiration curve. FIG. 3C translates the pump function curves into the curves of power output (W) vs. stroke volume (V), and shows the substantial difference in power output between inspiration and expiration, without accounting for any rate change. With rate increased during inspiration, the power output moves to a corresponding lower value.

Figure 4A:
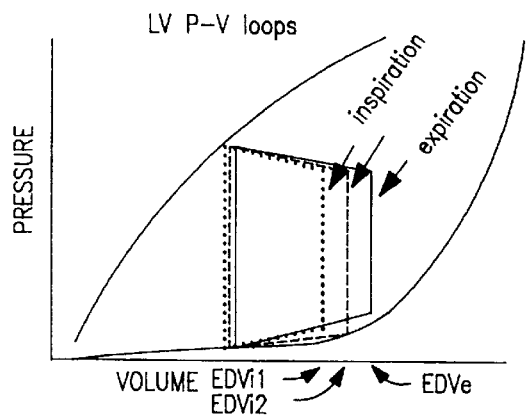
FIG. 4A shows pressure-volume loops for the left ventricle, illustrating the difference between inspiration and expiration.
Figure 4B:
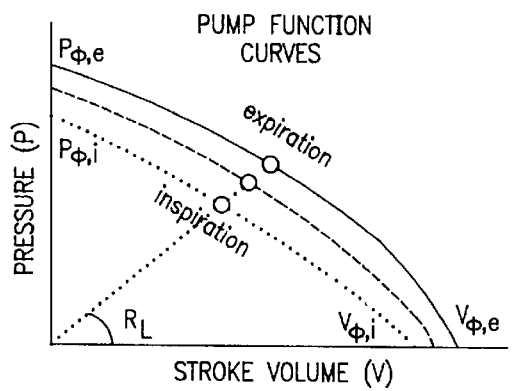
FIG. 4B shows pump function curves for the left ventricle.
Figure 4C:
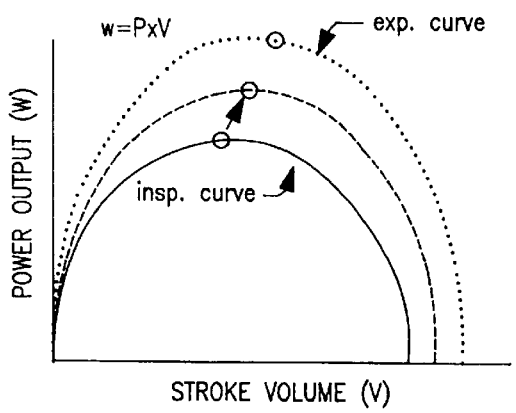
FIG. 4C shows power vs. stroke volume curves for the left ventricle.

Referring to FIGS. 4A through 4C, there is shown how the performance of the left ventricle differs from that of the right ventricle, as one compares the situation during inspiration to that of expiration. As stated above, the difference lies in the relative positions of the two ventricles with respect to the lungs. Whereas during inspiration the effective impedance of the lungs is lower and the right ventricle can fill to a greater volume, the left ventricle is downstream from the lung vessels which are expanding and thus retaining blood. Consequently, the LV does not receive as much blood, such that the end-diastolic volume is relatively less. This effect is enhanced by the large volume of the right ventricle and the mechanical coupling between the ventricles, which holds the left ventricle smaller when the right ventricle is greater. As seen in FIG. 4A, the expiration LV loop is larger than the inspiration LV loop, due to the filling of the lungs; EDVe is relatively greater than $EDV_{i-1}$. However, with increased heart rate, the lungs fill up more quickly, and enable the left ventricle to go a larger EDV, shown as $EDV_{i-2}$. Also, since the RV is not filling up as much, due to the shorter diastolic time, and total EDV of both ventricles is substantially constant, the LV is enabled to fill somewhat more. As is also seen in FIG. 4A, when rate is increased, the lungs can fill more quickly and thus their retaining effect is relatively minimized, resulting in a somewhat larger $EDV_{i-2}$. As seen in FIG. 4B, for the left ventricle the relative positions of the expiration and inspiration curves are switched compared to the right ventricle. Here, when rate is increased, the inspiration curve moves outward toward the expiration curve, resulting in an operation point which is closer to expiration. Note that the impedance of the peripheral vascular bed is substantially independent of the respiratory activity, such that the working points lies on the same RL line through the origin. The movement of the inspiration curve with an increase in rate is reflected in FIG. 4C, which shows that the difference in power output between inspiratory and expiratory beats is reduced by an increased heart rate during inspiration.

Figure 5:
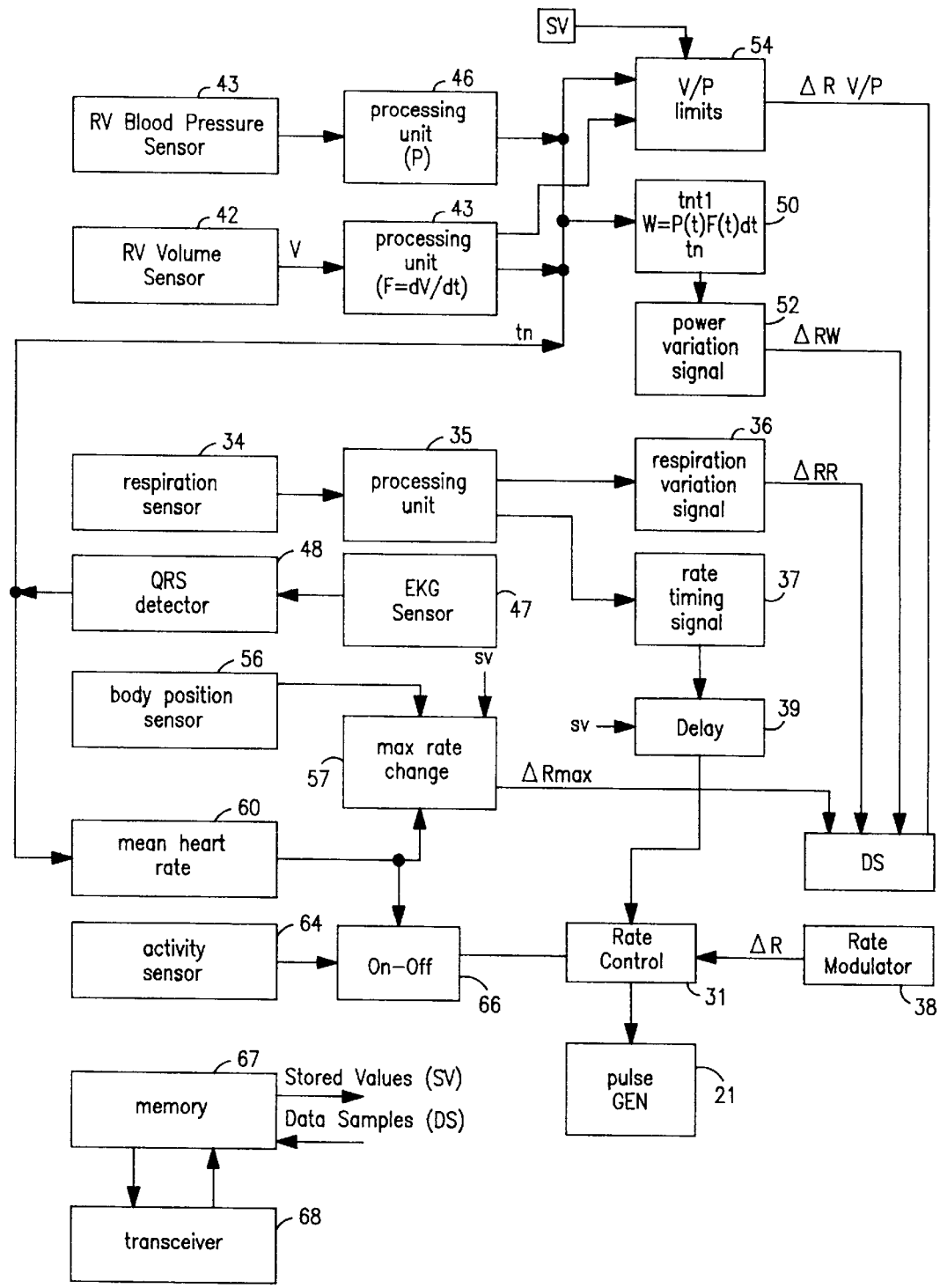
FIG. 5 is a schematic block diagram of a system in accordance with this invention for providing respiration-modulated pacing.

Referring now to FIG. 5, there is shown a system schematic of an implantable pacemaker device in accordance with this invention. In this schematic, operations are shown in block form, and can be carried out either by hardware or by software, as a matter of design choice. The pulse generator 21 is shown as receiving control signals from rate control block 31, which signals control phasic, or respiration modulation of rate (R). It is to be noted that control of other pace pulse parameters, as is conventional in the pacing art, is not shown in FIG. 5. The respiration sensor 34 provides signals which are processed at 35 to produce representations both of the amplitude of the respiration signal and the onset of inspiration. The timing signals indicative of onset of inspiration are coupled to rate timing signal generator 37. Block 37 provides a normally low output during expiration, but switches to a high level at the onset of inspiration. The signal from block 37 is passed through a suitable delay indicated at 39, and inputted to rate control block 31. A time delay between the onset of inspiration and the ensuing change in pacing rate is incorporated into the system in order to obtain optimum effect on heart function, and is suitably programmed for each individual user. Block 35 provides an amplitude signal which is representative of the cyclical amplitude variation of the respiration signal. The amplitude signal is processed at block 36 to provide a respiration variation signal, $^aR_R$, which is connected as one of several inputs into rate modulator 38. As is seen in the following discussion, a number of inputs are suitably employed to determine the magnitude of the rate modulation, $^aR$, e.g., the maximum increase in rate during the inspiration phase.

The output of RV volume sensor 42 is processed at 43, to provide a representation of flow (F), dV/dt. The flow signal is inputted into function block 50, which calculates for each cardiac cycle a representation of work, being an integral of the time functions of blood pressure and flow. The blood pressure signal is obtained from sensor 45, and is processed at 46 to provide the P(t) signal which is inputted to block 50. Further, EKG sensor 47 provides an output which is processed at block 48, to provide QRS signals and an indication of the time of each QRS. These timing signals are also inputted to block 50, to set and reset the integration function. Thus, once each cardiac cycle, block 50 produces an output representative of the work of the right ventricle. This work signal is processed at block 52 to provide a power variation signal, $^aR_W$ which is also connected to rate modulator 38. The $^aR_W$ signal is a measure of variations in the power output of the RV.

The F and P outputs are also connected to block 54, which monitors for maximum variations of F and P. These variations are compared to reference values which are represented as stored values (SV), for production of a third rate modulator signal, $^aR_{V/P}$, which is also inputted into rate modulator 38. If either volume or pressure are found to vary outside of predetermined limits, a $^aR_{V/P}$ signal is generated to modulate rate in a way to bring these values back to within limits. These three signals are also suitably compressed as data samples (DS) stored at block 67, for downloading as diagnostic data.

In addition to the three $^aR$ signals already identified, the system looks at other signals to determine the allowable maximum modulation, or $^aR_{max}$. A body position sensor 56 provides an output which is inputted to block 57, where a maximum rate change signal is generated. As discussed above, when the patient is at rest, the normal body provides for a maximum phasic change in rate with respect to respiration, whereas in times of activity, the variation is minimal. The body position sensor 56 determines when the patient is at rest, and inputs this into block 57. The output from the QRS sensor is also inputted to block 60, to determine a mean heart rate. The signals from blocks 56 and 60 are processed at 57 to provide an output signal ($^aR_{max}$) representative of the respiratory sinus arrhythmia curve, which correlates rate and phasic change in rate for a normal heart. The mean heart rate signal, along with an output from activity sensor 64, is also inputted to on-off signal block 66, to provide an on-off signal which is inputted to rate control block 31. Thus, if it is found that the mean heart rate exceeds a predetermined limit, or the activity sensor exceeds a respective predetermined limit, an off signal is generated and connected to rate control block 31, to inhibit phasic rate modulation.

The maximum amplitude of allowable rate modulation, $^aR_{max}$, is calculated by using the body position sensor and mean heart rate information to modify a stored value (SV). The amount of actual rate modulation, $^aR$, from 0 up to $^aR_{max}$, is calculated as a function of the outputs $^aR_R$, $^aR_W$, and $^aR_{V/P}$. The timing of the actual rate modulation is provided by the timing signal as generated at block 37, dependent upon the respiration information, and delayed at block 39. The rate modulator block 38 suitably comprises a software algorithm for processing the inputs and providing a $^aR$ modulation output, while the timing signal from block 39 controls the timing and wave shape of the rate control output. The rate control block 31 suitably comprises an algorithm for receiving the $^aR$ signal, and timing the change in rate, from 0 to a maximum of $^aR$, as a function of the respiration information. The increase of rate during inspiration can follow the respiration signal after a delay; or rate can simply be incremented by AR as long as the inspiration signal is high.

The system is flexible and can provide for phasic rate control which continually looks at beat-to-beat cardiac variations and adjusts phasic rate modulation toward maintaining more uniform power output. In pacemaker patients with a very low sinus rhythm, the mean pacing rate is suitably set high, so that the heart can follow up and down changes in rate during inspiration and expiration, respectively. For patients with a relatively high sinus rate, e.g., heart failure patients, the implanted pacemaker is suitably programmed only to increase heart rate during the inspiration phase; such pacing might be followed spontaneously by a compensatory decrease in sinus rhythm. As mentioned above, an alternative to direct pacing of the heart is to stimulate the Vagus nerve (or only the cardiac branch of the n.vagus) or the sympathetic nerve system. This causes a short duration decrease of heart rate, and should be timed for delivery during expiration. Any combination of direct cardiac pacing and vagus nerve stimulation may be employed for a given patient. Likewise, the modulation algorithm can be programmed to weigh the respective inputs in any desired manner. Further, the system can be programmed to be active only during rest, i.e., only if the body sensor and activity sensor outputs are below predetermined references.

Figure 6A:
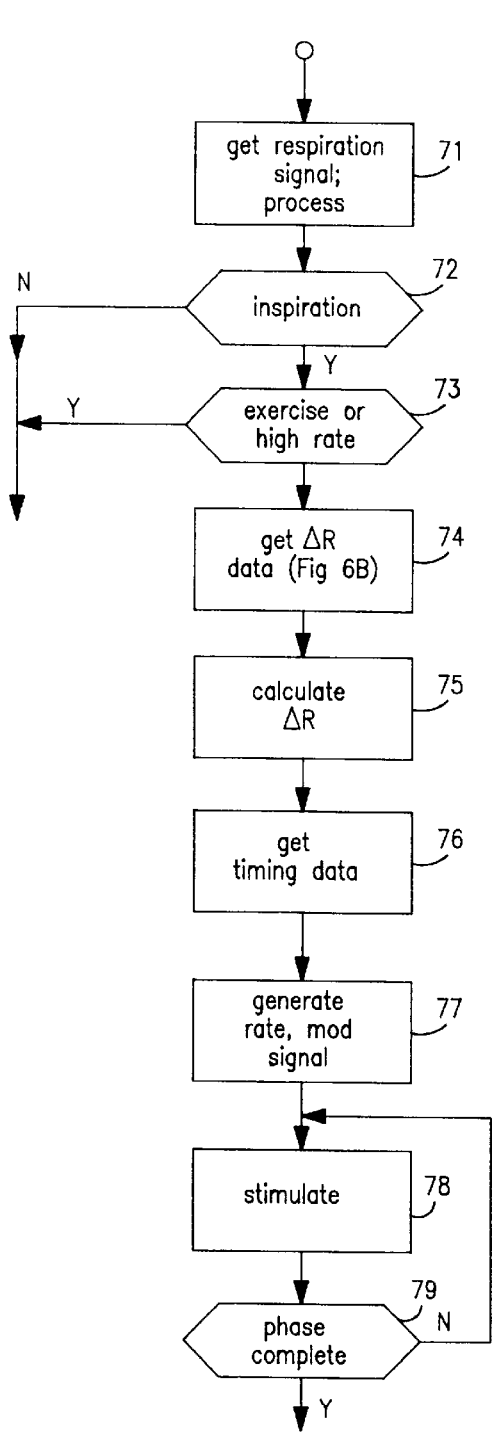
FIG. 6A is a flow diagram of the primary steps in the process of modulating pacing rate in accordance with patient respiration, as practiced in this invention.

Referring now to FIG. 6A, there is shown a flow diagram of the primary steps taken in modulating pacing rate in accordance with this invention. The routine is suitably carried out under software control every cardiac cycle. It is assumed that at the start of the routine the programmed stored values are available. At 71, the routine gets the respiration signals continuously provided by sensor 34, and processes them as indicated at unit 35. At 72, it is determined whether the patient is in the inspiration phase. If no, and assuming an embodiment where rate is only increased during inspiration and is not otherwise modulated, the routine exits. If yes, at 73 the exercise and high rate information from blocks 56 and 64 is examined. If the patient is in exercise or manifests a high rate above a given level, this means that there should be no phasic modulation, and again the routine exits. Assuming conditions for phasic modulation, at 74 the routine gets the $^aR$ data, as shown in more detail in FIG. 6B. At 75, the value of $^aR$ is calculated, as shown at block 38 in FIG. 5. At 76, the timing data is obtained, and at 77 the rate modulation signal is generated as a function of the calculated $^aR$ value and the timing data. Thus, step 77 involves an algorithm for generating the rate modulation signal to provide both the change in rate and the timing with respect to the onset of inspiration. At 78 the stimulation step is carried out, i.e., a stimulus pulse is delivered at a modulated rate. At 79, it is determined whether the phase is complete, i.e., whether inspiration is still ongoing and rate modulation should continue. If the phase is not complete, the routine returns and continues stimulation at 78, until the phase is complete. While this flow diagram illustrates modulation limited to increasing rate during inspiration, as is noted above rate can also be decreased during expiration.

Figure 6B:
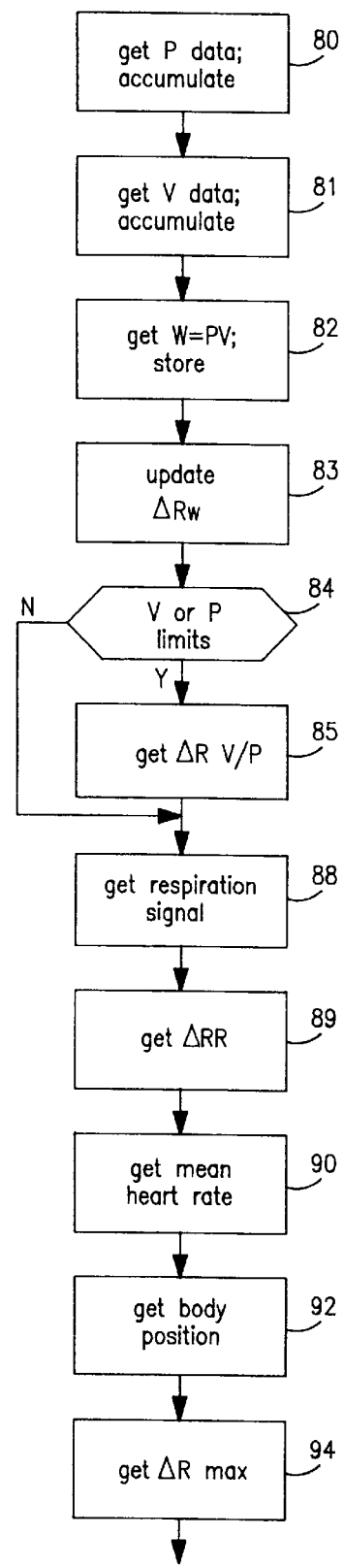
FIG. 6B is a flow diagram of the specific steps of obtaining parameter data to be used in calculating respiration phasic rate variations.

Referring to FIG. 6B, there is shown a flow diagram illustrating the detailed steps of determining the data which is used at block 75 of FIG. 6A to obtain the $^aR$ value. At 80, the pressure data is obtained and accumulated. At 81, the RV volume data is obtained and accumulated. At 82, the work signal, as indicated above in relation to block 50 of FIG. 5, is obtained. Following this, at block 83 the parameter $^aR_W$ is updated on the basis of the last computed W value. Then, at 84, the volume and pressure signals are examined to see whether either has exceeded predetermined limits; if yes, an appropriate $^aR_{V/P}$ signal is generated at 85. At 88, the respiration signal is obtained, and at 89 it is processed to get the respiration variation signal, $^aR_R$. At 90, the mean heart rate is obtained, and at 92 the body position signal is obtained; this data is utilized at 94 to determine the value of $^aR_{max}$.

There has been illustrated a closed loop system for pacing the heart at a modulated rate so as to minimize variations in ventricular power output. In a preferred embodiment, the system tracks patient respiration, and increases rate during inspiration relative to expiration, so as to lessen changes in ventricular cyclical power output.

What is claimed is:

1. A system for respiration modulated pacing, comprising:
    pulse generator means for generating and delivering pacing pulses to one of a vagus nerve and sympathetic nerve system to control the beat rate of a patient's heart; and
    rate control means for controlling a pacing rate of said pacing pulses, said rate control means further comprising:
        respiration means for obtaining respiration signals representative of patient respiration, and modulation means for developing rate modulation signals for controlling said pacing rate to change as a function of said respiration signals and to increase during the patient's inspiration phase relative to the pacing rate during the patients expiration phase.

2. The system as described in claim 1, wherein said respiration means comprises sensing means for sensing signals representative of the patient's intrathoracic pressure.

3. The system as described in claim 1, wherein said respiration means comprises signal means for providing a signal indicating the onset of patient inspiration, and said modulation means comprises timing means for timing rate modulation signals to increase pacing rate in response to a said indicated inspiration onset.

4. The system as described in claim 3, wherein said timing means comprises delay means for delaying the increase in pacing rate following a said indicated inspiration onset.

5. The system as described in claim 1, wherein said modulation means comprises amplitude means for controlling an amplitude of pacing rate change and timing means for controlling the timing of said pacing rate change relative to the patient's Inspiration phase and expiration phase of said patient's respiratory cycle.

6. The system as described in claim 5, wherein said amplitude means comprises cardiac work means for determining a measure of cyclical cardiac work and for controlling said amplitude as a function of said work measure.

7. The system as described in claim 5, wherein said amplitude means comprises volume means for determining a measure of the end-diastolic volume of a ventricle of said patient and for controlling said amplitude as a function of said volume measure.

8. The system as described in claim 5, wherein said amplitude means comprises pressure means for determining a measure of the blood pressure relating to a ventricle of said patient and for controlling said amplitude as a function of said blood pressure measure.

9. The system as described in claim 5, wherein said amplitude means comprises maximum rate change means for limiting the amplitude of pacing rate change during said respiratory cycle.

10. The system as described in claim 9, wherein said maximum rate change means comprises body position sensor means for sensing the patient's body position and for limiting said amplitude of pacing rate change as a function of said sensed body position.

11. The system as described in claim 9, wherein said maximum rate change means comprises heart rate means for determining a measure of the patient's heart rate and for limiting said amplitude of pacing rate change as a function of said heart rate measure.

12. The system as described in claim 5, wherein said respiration means comprises means for determining the onset of patient inspiration, and said timing means comprises means for enabling said modulation means to increase said pacing rate in response to a said indicated inspiration onset.

13. The system as described in claim 12, wherein said timing means comprises delay means for delaying enablement of said modulation means relative to said inspiration onset.

14. The system as described in claim 1, further comprising means for determining a measure of patient activity, and inhibit means for inhibiting said modulation means from changing said pacing rate as a function of respiration signals when said activity measure exceeds a predetermined reference level.

15. A system for pacing a patient's heart, comprising:

pulse generator means for generating and delivering pace pulses to one of a vagus nerve and sympathetic nerve system of said patient;

rate control means for controlling a pacing rate at which said pulse generator means generates and delivers pace pulses;

respiration means for obtaining respiration signals representative of patient's respiration, and said rate control means comprising modulation means for modulating said pacing rate as a function of said respiration signals.

16. The system as described in claim 15, wherein said respiration means comprises means for determining patient inspiration and expiration, and said modulation means comprises means for increasing said pacing rate during inspiration relative to pacing rate during expiration.

17. The system as described in claim 15, wherein said respiration means comprises means for obtaining signals representative of patient inspiration, and said modulation means comprises means for increasing said pacing rate in response to said signals representative of patient inspiration.

18. The system as described in claim 17, further comprising rate means for detecting patient sinus rate, and wherein said modulation means comprises means for overdriving said sinus rate during periods of patient inspiration.

19. The system as described in claim 15, further comprising power means for determining a measure of cardiac power output, and wherein said modulation means further comprises means for adjusting pacing rate as a function of said cardiac power output measure.

20. The system as described in claim 15, further comprising activity means for obtaining activity representations of patient activity or position, and wherein said modulation means further comprises means for adjusting pacing rate as a function of said activity representations.

21. The system as described in claim 15, further comprising pressure means for obtaining pressure representations of the patient's ventricular pressure, and wherein said modulation means further comprises means for adjusting pacing rate as a function of said pressure representations.

22. The system as described in claim 15, further comprising volume means for obtaining volume representations of the patient's ventricular volume, and wherein said modulation means further comprises means for adjusting pacing rate as a function of said volume representations.

23. An implantable system for varying a patient's heart rate as a function of the patient's respiratory cycles, comprising:

a stimulus generator for generating stimulus signals at a rate;

delivery means for delivering said stimulus signals to one of a vagus nerve and sympathetic nerve system within said patient and to modulate the patient's heart rate;

respiration means for obtaining respiration signals representative of the patient's respiratory cycles; and control means for controlling said stimulus generator to generate said stimulus signals as a function of said respiration signals.

24. The system as described in claim 23, wherein said respiration means comprises means for determining periods of patient expiration, and said control means has means for controlling said stimulus generator to generate stimulus signals during an expiration period.

25. The system as described in claim 23, wherein said respiration means comprises means for determining periods of patient inspiration, and said control means comprises means for increasing the rate of said stimulus signals during periods of inspiration.

26. A method of pacing a patient to provide a respiration-modulated heart rate, comprising:

obtaining respiration signals representative of the inspiratory and expiratory phases of the patient's respiratory cycle, generating phasic rate control signals as a function of at least one of said inspiratory and expiratory phases, generating stimulus pulses at a rate controlled by said phasic rate control signals, and delivering said phasic rate controlled stimulus pulses to one of the vagus nerve and sympathetic nerve system to pace the patient's heart at a relatively higher rate during said inspiratory phase compared to said expiratory phase.

27. The method of pacing as described in claim 26, further comprising the steps of obtaining volume signals representative of the patient's right ventricular volume, and generating said phasic rate control signals as a function of said volume signals.

28. The method of pacing as described in claim 26, further comprising the steps of obtaining pressure signals representative of the patient's right ventricular blood pressure, and generating said phasic rate control signals as a function of said pressure signals.

\* \* \* \* \*